(12) United States Patent
Young et al.

(10) Patent No.: US 12,257,276 B2
(45) Date of Patent: Mar. 25, 2025

(54) LACTOBACILLUS AMYLOVORUS LAM1345 ISOLATE, COMPOSITION INCLUDING THE SAME AND USE THEREOF

(71) Applicant: SYNBIO TECH INC., Kaohsiung (TW)

(72) Inventors: San-Land Young, Kaohsiung (TW); Hau-Yang Tsen, Taichung (TW); Chen-Ying Hung, Hsinchu County (TW); Yu-Cheng Chiang, Taichung (TW)

(73) Assignee: SYNBIO TECH INC., Kaohsiung (TW)

( * ) Notice: Subject to any disclaimer, the term of this patent is extended or adjusted under 35 U.S.C. 154(b) by 582 days.

(21) Appl. No.: 17/606,977

(22) PCT Filed: Jun. 30, 2021

(86) PCT No.: PCT/CN2021/103607
§ 371 (c)(1),
(2) Date: Oct. 27, 2021

(87) PCT Pub. No.: WO2022/151669
PCT Pub. Date: Jul. 21, 2022

(65) Prior Publication Data
US 2022/0370522 A1   Nov. 24, 2022

(30) Foreign Application Priority Data

Jan. 12, 2021 (CN) .......................... 202110037395.2

(51) Int. Cl.
| | | |
|---|---|---|
| *A61K 35/747* | (2015.01) | |
| *A61K 35/745* | (2015.01) | |
| *C12N 1/20* | (2006.01) | |
| *C12R 1/225* | (2006.01) | |

(52) U.S. Cl.
CPC .......... *A61K 35/747* (2013.01); *A61K 35/745* (2013.01); *C12N 1/205* (2021.05); *C12R 2001/225* (2021.05)

(58) Field of Classification Search
CPC .... A61K 35/747; A61K 35/745; C12N 1/205; C12R 2001/225
See application file for complete search history.

(56) References Cited

U.S. PATENT DOCUMENTS 8,906,668 B2 * 12/2014 Henn et al. ............ A61K 35/74
435/252.4

* cited by examiner

*Primary Examiner* — Louise W Humphrey
*Assistant Examiner* — John Paul Selwanes
(74) *Attorney, Agent, or Firm* — HSML P.C.

(57) ABSTRACT

Disclosed herein is an isolated strain of *Lactobacillus amylovorus* LAM1345, which is deposited at Deutsche Sammlung von Mikroorganismen and Zellkulturen GmbH under an accession number DSM 33510. Also disclosed herein are a composition including the isolated strain of *Lactobacillus amylovorus* LAM1345 for reducing trimethylamine (TMA) and/or trimethylamine-n-oxide (TMAO) levels, and use of the isolated strain of *Lactobacillus amylovorus* LAM1345 for treating a disease associated with at least an elevated one of TMA and TMAO levels in a subject.

3 Claims, 3 Drawing Sheets

Specification includes a Sequence Listing.

LACTOBACILLUS AMYLOVORUS LAM1345 ISOLATE, COMPOSITION INCLUDING THE SAME AND USE THEREOF

CROSS-REFERENCE TO RELATED APPLICATION

This application is a national phase entry application of PCT International Application No. PCT/CN2021/103607 filed on Jun. 30, 2021, which claims priority of Chinese Invention patent application No. 202110037395.2, filed on Jan. 12, 2021. The entire content of each of the international and Chinese patent applications is incorporated herein by reference.

FIELD

The present disclosure relates to an isolated strain of *Lactobacillus amylovorus* LAM1345, which has been deposited at Deutsche Sammlung von Mikroorganismen and Zellkulturen GmbH under an accession number DSM 33510. The present disclosure also relates to a composition including the isolated strain of *Lactobacillus amylovorus* LAM1345, and use of the composition for treating a disease associated with at least an elevated one of trimethylamine (TMA) and trimethylamine-n-oxide (TMAO) levels.

BACKGROUND

Trimethylamine-n-oxide (TMAO) [chemical formula: $(CH_3)_3NO$] is an organic metabolite classified as an amine oxide. In recent years, accumulation of TMAO in the human body has been reported as one of the main factors which causes or accelerates the course of various diseases. Choline, when ingested in an excess amount, is metabolized in the gastrointestinal tract into trimethylamine (TMA), which is then transported to the liver through the blood circulatory system and oxidized by hepatic flavin monooxygenase 3 (FMO3) into TMAO. Accumulation of TMAO induces a series of inflammatory reactions (e.g., accumulation of macrophages in blood vessel walls, platelet aggregation, etc.) which might lead to various diseases collectively referred to as "diseases associated with elevated TMA and/or TMAO levels" such as, among others, kidney diseases, diabetes mellitus, obesity, trimethylaminuria (also referred to as fish odor syndrome (FOS)), cardiovascular diseases.

It has been reported that for treating the abovementioned diseases, apart from using conventional treatment methods, reducing the levels of TMA and TMAO in the patients' blood may be a feasible option. Drugs used in conventional treatment methods to lower the levels of TMA and TMAO include 3,3-dimethyl-1-butanol (DMB), acetylsalicylic acid, FMO3 inhibitors, TMA lyase inhibitors, antibiotics, antimicrobials, antiplatelet agents, and sequestering agents of TMA and/or TMAO. However, these drugs exhibit unsatisfactory curative effect, which is mainly due to individual differences of the patients, and the serious side effects and adverse effects of the drugs on the patients. Therefore, those skilled in the art still strive to develop an effective way to reduce the level of TMA and/or TMAO without causing undesirable side effects.

Lactic acid bacteria (LAB) are gram-positive bacteria that produce lactic acid as a major metabolite end product of carbohydrate fermentation, and are ubiquitously found in dairy products, pickled food, and gastrointestinal tract mucosa of humans and animals. LAB are conferred with the generally recognized as safe (GRAS) status, and are widely used as probiotics. LAB have been reported to exert effects such as inhibiting the growth of pathogens in the gastrointestinal tract, alleviating lactose intolerance, improving immunoregulatory function, providing anti-cancer properties, lowering blood pressure, etc. Examples of common LAB include *Lactobacillus* spp., *Lactococcus* spp., *Pediococcus* spp., *Streptococcus* spp., *Enterococcus* spp., etc.

Previous studies demonstrated that certain strains of LAB have the effect of reducing the TMAO level in mouse serum. For example, as reported in Qiu L. et al. (2018), *Food Funct.*, 9:4299-4309, in BALE/c mice administered separately with different strains of LAB, i.e., *Lactobacillus plantarum* ZDY01, *Lactobacillus plantarum* ZDY04, *Lactobacillus rhamnosus* ZDY9, *Lactobacillus casei* ZDY8, and *Lactobacillus bulgaricus* ZDY5, only *Lactobacillus plantarum* ZDY04 can effectively reduce the TMAO level in the mice serum. In addition, Qiu L. et al. also disclosed that when C57BL/6J ApoE$^{-/-}$ mice (i.e., a mouse model for atherosclerosis) were administered with *Lactobacillus plantarum* ZDY04 and then subjected to measurement of the TMAO level in the mice serum and observation of atherosclerotic lesion formation, the level of TMAO in the mice serum was reduced and the atherosclerotic lesions in the mice were improved. Thus, *Lactobacillus plantarum* ZDY04 is expected to be useful for treating and preventing arteriosclerosis and atherosclerotic cardiovascular diseases.

In spite of the aforesaid, there is still a need to screen a new species and/or strain of LAB that can reduce the level of TMA and TMAO in patients' blood and can exhibit satisfactory efficacy in treating diseases associated with elevated TMA and/or TMAO levels.

SUMMARY

Therefore, in a first aspect, the present disclosure provides an isolated strain of *Lactobacillus amylovorus* LAM1345 which can alleviate at least one of the drawbacks of the prior art.

The isolated strain of *Lactobacillus amylovorus* LAM1345 is deposited at Deutsche Sammlung von Mikroorganismen and Zellkulturen GmbH under an accession number DSM 33510.

In a second aspect, the present disclosure provides a composition for reducing trimethylamine (TMA) and/or trimethylamine-n-oxide (TMAO) levels, which can alleviate at least one of the drawbacks of the prior art, and which includes the aforesaid isolated strain of *Lactobacillus amylovorus* LAM1345.

In a third aspect, the present disclosure provides a method for treating a disease associated with at least an elevated one of TMA and TMAO levels, which can alleviate at least one of the drawbacks of the prior art, and which includes administering to a subject in need thereof a pharmaceutical composition containing the abovementioned isolated strain of *Lactobacillus amylovorus* LAM1345.

In a fourth aspect, the present disclosure provides use of the aforesaid isolated strain of *Lactobacillus amylovorus* LAM1345 in the manufacture of a medicament for treating a disease associated with at least an elevated one of TMA and TMAO levels in a subject. Such use can alleviate at least one of the drawbacks of the prior art.

In a fifth aspect, the present disclosure provides the aforesaid isolated strain of *Lactobacillus amylovorus* LAM1345 for use in the treatment of a disease associated with at least an elevated one of TMA and TMAO levels in a subject. Such strain can alleviate at least one of the drawbacks of the prior art.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

It is to be understood that, if any prior art publication is referred to herein, such reference does not constitute an admission that the publication forms a part of the common general knowledge in the art, in China or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

By virtue of research, the applicants surprisingly found that a strain of *Lactobacillus amylovorus*, which is isolated from corn and assigned with a name of *Lactobacillus amylovorus* LAM1345 through characterization, is capable of reducing trimethylamine (TMA) and/or trimethylamine-n-oxide (TMAO) levels in a subject, and hence is expected to be effective in treating a disease associated with at least an elevated one of TMA and TMAO levels.

Therefore, the present disclosure provides an isolated strain of *Lactobacillus amylovorus* LAM1345, which has been deposited at the Bioresource Collection and Research Center (BCRC) of the Food Industry Research and Development institute (FIRDI), Taiwan, China under an accession number BCRC 910996 since Apr. 23, 2020, and has also been deposited at the Deutsche Sammlung von Mikroorganismen and Zellkulturen (DSMZ) GmbH under an accession number DSM 33510 since Apr. 27, 2020 in accordance with the Budapest Treaty.

According to the present disclosure, the isolated strain of *Lactobacillus amylovorus* LAM1345 may be live cells or dead cells, concentrated or non-concentrated, a liquid, a paste, a semi-solid, a solid (e.g., a pellet, a granule, or a powder), and may be heat-inactivated, frozen, dried, or freeze-dried (e.g., may be in freeze-dried form or spray/fluid bed dried form). In an exemplary embodiment, the isolated strain of *Lactobacillus amylovorus* LAM1345 is in a liquid form.

The present disclosure also provides a composition for reducing TMA and/or TMAO levels, which includes the aforesaid isolated strain of *Lactobacillus amylovorus* LAM1345.

According to the present disclosure, the composition may further include a probiotic selected from the group consisting of *Lactobacillus fermentum*, *Lactobacillus plantarum*, *Lactobacillus acidophilus*, *Lactobacillus brevis*, *Lactobacillus buchneri*, *Lactobacillus kefir*, *Lactobacillus bulgaricus*, *Lactobacillus casei*, *Lactobacillus crispatus*, *Lactobacillus delbrueckii*, *Lactobacillus gasseri*, *Lactobacillus helveticus*, *Lactobacillus johnsonii*, *Lactobacillus jensenii*, *Lactobacillus kefiranofaciens*, *Lactobacillus mali*, *Lactobacillus paracasei*, *Lactobacillus pentosus*, *Lactobacillus reuteri*, *Lactobacillus rhamnosus*, *Lactobacillus sake*, *Lactobacillus salivarius*, *Bifidobacterium adolescentis*, *Bifidobacterium animalis*, *Bifidobacterium breve*, *Bifidobacterium infantis*, *Bifidobacterium longum*, and a combination thereof. In an exemplary embodiment, the composition further includes *Lactobacillus fermentum* LF1143 (deposited at the DSMZ GmbH under an accession number DSM 33124) and *Lactobacillus plantarum* LP1145 (deposited at the DSMZ GmbH under an accession number DSM 33125).

As used herein, the terms "probiotic" and "probiotic microbes" are used interchangeably, and refer to preparations of live microorganisms. These microorganisms may remain and survive in the gastrointestinal tract after ingestion by a subject, and can exert a desired effect (e.g., preventive or therapeutic effect, etc.).

In certain embodiments, the composition of the present disclosure may be formulated as a food product using a standard technique well known to one of ordinary skill in the art. For example, the composition may be directly added to an edible material or may be used to prepare an intermediate composition (e.g., a premix) suitable to be subsequently added to the edible material.

As used herein, the term "food product" refers to any article or substance that can be ingested by a subject into the body thereof. Examples of the food product may include, but are not limited to, fluid milk products (e.g., milk and concentrated milk), fermented milk (e.g., yogurt, sour milk, and frozen yogurt), milk powder, ice cream, cream cheese, dry cheese, soybean milk, vegetable fruit juice, fruit juice, sport drinks, confectionery, jelly, candies, health foods, animal feeds, feed additives, and dietary supplements.

In certain embodiments, the composition of the present disclosure may be formulated as a pharmaceutical composition. The pharmaceutical composition may further include a pharmaceutically acceptable carrier, and may be made into a dosage form suitable for oral administration using technology well-known to those skilled in the art. Examples of the oral dosage form include, but are not limited to, sterile powder, tablets, troches, lozenges, pellets, capsules, dispersible powder, granule, solutions, suspensions, emulsions, drops, syrup, elixirs, slurry, and the like.

Examples of the pharmaceutically acceptable carrier may include, but are not limited to, solvents, buffers, emulsifiers, suspending agents, decomposers, disintegrating agents, dispersing agents, binding agents, excipients, stabilizing agents, chelating agents, diluents, gelling agents, preservatives, wetting agents, lubricants, absorption delaying agents, liposomes, and the like. The choice and amount of the pharmaceutically acceptable carrier are within the expertise of those skilled in the art.

Since the isolated strain of *Lactobacillus amylovorus* LAM1345 of the present disclosure has been verified to effectively inhibit the conversion of choline to TMA and the formation of TMAO through in vivo animal testing, the applicants believe that the isolated strain of *Lactobacillus amylovorus* LAM1345 of the present disclosure has a high potential to be developed for treatment of diseases associated with at least an elevated one of TMA and TMAO levels.

Therefore, the present disclosure provides a method for treating a disease associated with at least an elevated one of TMA and TMAO levels, which includes administering to a subject in need thereof a pharmaceutical composition containing the aforesaid isolated strain of *Lactobacillus amylovorus* LAM1345.

The present disclosure also provides use of the aforesaid isolated strain of *Lactobacillus amylovorus* LAM1345 in the manufacture of a medicament for treating a disease associated with at least an elevated one of TMA and TMAO levels in a subject. In certain embodiments, the medicament is in a dosage form for oral administration.

Moreover, the present disclosure provides the aforesaid isolated strain of *Lactobacillus amylovorus* LAM1345 for use in the treatment of a disease associated with at least an elevated one of TMA and TMAO levels in a subject.

As used herein, the term "treating" or "treatment" means preventing, reducing, alleviating, ameliorating, relieving, or controlling one or more clinical signs of a disease or disorder, and lowering, stopping or reversing the progression of the severity of the condition(s) or symptom(s) that is being treated.

As used herein, the term "administering" or "administration" means introducing, providing or delivering a pre-determined active ingredient to a subject by any suitable routes to perform its intended function.

As used herein, the term "subject" refers to any animal of interest, such as humans, monkeys, cows, sheep, horses, pigs, goats, dogs, cats, mice, and rats. In certain embodiments, the subject is a human.

According to the present disclosure, examples of the disease associated with at least an elevated one of TMA and TMAO levels may include, but are not limited to, kidney diseases, diabetes mellitus, obesity, trimethylaminuria (also known as fish odor syndrome (FOS)), cardiovascular diseases, and cancer.

The dose and frequency of administration of the composition of the present disclosure may vary depending on the following factors: the severity of the illness or disorder to be treated, routes of administration, and age, physical condition and response of the subject to be treated. In general, the composition may be administered in a single dose or in several doses.

The present disclosure will be further described by way of the following examples. However, it should be understood that the following examples are intended solely for the purpose of illustration and should not be construed as limiting the present disclosure in practice.

EXAMPLES

General Experimental Materials:
1. Experimental Mice

Female C57BL/6J mice (5 weeks old, with a body weight of approximately 23 g±2 g) used in the following experiments were purchased from National Laboratory Animal Center, Taiwan, China. All the experimental mice were housed in an animal room under the following laboratory conditions: an alternating 12-hour light and 12-hour dark cycle, a temperature maintained at 23° C.±2° C., and a relative humidity maintained at 50% to 70%. The mice were provided with water and fed ad libitum with a choline-deficient diet (Diet TD88052, Harlan Teklad, Madison, WI, USA). All experimental procedures involving the experimental mice were in compliance with the legal provision of the Animal Protection Act of Taiwan, China, and were carried out according to the guidelines of the Animal Care Committee of the Council of Agriculture, Taiwan, China.

Example 1. Screening and Characterization of
*Lactobacillus amylovorus* LAM1345 Strain Experimental Materials and Procedures:
A. Source and Isolation of *Lactobacillus amylovorus* LAM1345 Strain Corns purchased from a local traditional market were used as a sample source, and an isolated strain of *Lactobacillus amylovorus* LAM1345 was screened from the sample source using Lactobacilli MRS (De Man, Rogosa and Sharpe) Agar (BD Difco™, USA).

In order to verify the *Lactobacillus amylovorus* LAM1345 strain, the following experiments were conducted.

B. Preliminary Characterization of *Lactobacillus Amylovorus* LAM1345 Strain

Preliminary tests performed to characterize the *Lactobacillus amylovorus* LAM1345 strain include Gram staining, morphological observation, motility test, catalase reaction, formation of endospores, growth under aerobic and anaerobic conditions, and acid and bile salt tolerance assay. These preliminary tests are commonly and routinely used in the art, and the details thereof are omitted herein for the sake of brevity.

Results obtained from the abovementioned preliminary tests show that the *Lactobacillus amylovorus* LAM1345 strain is Gram-positive, non-motile, catalase-negative, and grows under anaerobic conditions without forming endospores, and has good acid tolerance and bile salt tolerance. The acid tolerance and bile salt tolerance were demonstrated by a survival rate of higher than 60% after cultivation in phosphate-buffered saline (PBS) at a pH ranging from 2 to 3 for 1 hour, and a survival rate of up to 93% after cultivation in Lactobacilli MRS Broth (ED Difco™, USA) containing 0.3% (v/v) bovine bile, respectively.

C. 16S rDNA Sequence Analysis

Genomic DNA of the *Lactobacillus amylovorus* LAM1345 strain was extracted using the Genomic DNA Mini Kit (Manufacturer: Geneaid Biotech Ltd.; Catalogue No: GB100/GB300). The thus obtained genomic DNA was used as a template and was subjected to polymerase chain reaction (PCR) that was performed on a Biometra TOne thermal cycler (Manufacturer: Analytik Jena GmbH, Germany) using a designed primer pair specific for 16S ribosomal DNA (rDNA) and the reaction conditions shown in Table 1, thereby obtaining a PCR product having a size of approximately 1500 bp.

TABLE 1

| Contents | | Volume (μL) |
|---|---|---|
| Genomic DNA of *Lactobacillus amylovorus* LAM1345 strain (10 ng) | | 1 |
| 16S rDNA-specific primer pair | Forward primer (10 μM): 5'-agagtttgatcctggctcag-3' (SEQ ID No: 1) | 0.5 |
| | Reverse primer (10 μM): 5'-ggttaccttgttacgact-3' (SEQ ID No: 2) | 0.5 |

TABLE 1-continued

| Contents | Volume (μL) |
| --- | --- |
| Taq DNA Polymerase Master Mix RED (2X) (Ampliqon) | 10 |
| Deionized water | 8 |

Operation conditions: denaturation at 94° C. for 5 min, followed by 30 cycles of the following reactions: denaturation at 94° C. for 60 sec, primer annealing at 50° C. for 60 sec, and extension at 72° C. for 60 sec; and lastly, elongation at 72° C. for 7 min.

The resultant PCR product was subjected to a 2% agarose gel electrophoresis analysis for molecular weight verification. Thereafter, the purified PCR product was verified by sequencing analysis which was entrusted to Genomics BioSci & Tech Co., Ltd., Taiwan, China, so as to obtain the 16S rDNA sequence (SEQ ID No: 3) of the *Lactobacillus amylovorus* LAM1345 strain. Through comparison with nucleotide sequences obtained from the NCBI's gene database using BLAST algorithm, it was found that the 16S rDNA sequence of the *Lactobacillus amylovorus* LAM1345 strain has 99.9% identity to a part of the 16S rDNA sequence (GenBank accession number: AY944408.1) of *Lactobacillus amylovorus* strain DSM 20531.

D. Leader Peptidase A (lepA) Gene Sequence Analysis

Genomic DNA of the *Lactobacillus amylovorus* LAM1345 strain obtained according to the procedures as described in the section entitled "C. 16S rDNA sequence analysis" above was used as a template and was subjected to PCR using a designed primer pair specific for leader peptidase A (lepA) gene and the reaction conditions shown in Table 2. A PCR product having a size of approximately 1163 bp was obtained.

TABLE 2

| Contents | | Volume (μL) |
| --- | --- | --- |
| Genomic DNA of *Lactobacillus amylovorus* LAM1345 strain (50 ng) | | 1 |
| lepA gene-specific primer pair | Forward primer (10 μM): 5'-ggdcacgtrgayttytcwtayga-3' (SEQ ID No: 4) | 0.5 |
| | Reverse primer (10 μM): 5'-gcatavccyttngtdrawgactt-3' (SEQ ID No: 5) | 0.5 |
| dNTPs (10 mM) | | 0.5 |
| 10X buffer | | 2.5 |
| Taq DNA Polymerase (Protech Technology Enterprise Co., Ltd., Taiwan, China) | | 0.5 |
| MgCl$_2$ (50 mM) | | 1 |
| Deionized water | | 18.5 |

Operation conditions: denaturation at 94° C. for 4 min, followed by 35 cycles of the following reactions: denaturation at 94° C. for 60 sec, primer annealing at 50° C. for 75 sec, and extension at 72° C. for 60 sec; and lastly, elongation at 72° C. for 7 min.

The resultant PCR product was subjected to a 2% agarose gel electrophoresis analysis for molecular weight verification.

Thereafter, the PCR product was verified by sequencing analysis which was entrusted to Genomics BioSci & Tech Co., Ltd., Taiwan, China, so as to obtain the lepA gene sequence (SEQ ID No: 6) of the *Lactobacillus amylovorus* LAM1345 strain. Through comparison with the data in the NCBI's gene database using BLAST algorithm, it was found that the lepA gene sequence of the *Lactobacillus amylovorus* LAM1345 strain has merely 99.6% identity to the lepA gene sequence (corresponding to nucleotide residues 29946 to 30954 of the nucleotide sequence having GenBank accession number: AZCM01000018.1) of *Lactobacillus amylovorus* DSM 20531$^T$, suggesting that the *Lactobacillus amylovorus* LAM1345 strain characterized thus far by the applicants is different from conventionally known strains of *Lactobacillus amylovorus*.

Based on the aforementioned characterization results as described in aforesaid sections entitled "B. Preliminary characterization of *Lactobacillus amylovorus* LAM1345 strain" to "D. Leader peptidase A (lepA) gene sequence analysis", the applicants believe that the *Lactobacillus amylovorus* LAM1345 strain is a novel strain of *Lactobacillus amylovorus*. As such, *Lactobacillus amylovorus* LAM1345 has been deposited at the Biosource Collection and Research Center (BCRC) of the Food Industry Research and Development Institute (FIRDI) (No. 331, Shih-Pin Rd., Hsinchu City 300, Taiwan, China) under accession number BCRC 910996 since Apr. 23, 2020, and has also been deposited at the Deutsche Sammlung von Mikroorganismen und Zellkulturen (DSMZ) GmbH under an accession number DSM 33510 since Apr. 27, 2020 in accordance with the Budapest Treaty.

Example 2. Evaluation of the Effect of *Lactobacillus amylovorus* LAM1345 on the Formation of Trimethylamine-n-Oxide (TMAO)

Experimental Materials:
A. Preparation of Liquid Lactic Acid Bacterial (LAB) Culture The thus verified isolated strain of *Lactobacillus amylovorus* LAM1345, as well as two other *Lactobacillus* spp., was subjected to the following experiments. The relevant information regarding each of the LAB strains (including international depositary authority, accession number and date of deposit) is listed in Table 3 below.

TABLE 3

| LAB strains | International depositary authority and accession number | Date of deposit |
| --- | --- | --- |
| *Lactobacillus amylovorus* LAM1345 | BCRC of FIRDI, BCRC 910996 | Apr. 23, 2020 |
| | DSMZ, DSM 33510 | Apr. 27, 2020 |
| *Lactobacillus fermentum* LF1143 | BCRC of FIRDI, BCRC 910896 | May 14, 2019 |
| | DSMZ, DSM 33124 | May 16, 2019 |
| *Lactobacillus plantarum* LP1145 | BCRC of FIRDI, BCRC 910897 | May 14, 2019 |
| | DSMZ, DSM 33125 | May 16, 2019 |

First, a respective one of the three LAB strains as described above was inoculated into 1.0 L of a Lactobacilli MRS Broth (BD Difco™, USA), and was then cultured at a temperature of 37° C. for 8 to 10 hours to obtain a respective one of LAB cultures. Next, each of the LAB cultures was subjected to centrifugation at 4° C. under a speed of 12000 rpm for 30 minutes to form supernatant and pellet fractions. After that, the supernatant was poured off, and then the pellet was washed and resuspended in an appropriate amount of PBS, so as to obtain a liquid LAB culture having a concentration ranging from $10^8$ CFU/mL to $10^{10}$ CFU/mL, which was determined using a plate counting medium (Manufacturer: BD Difco™, USA). The respective one of the resultant liquid LAB cultures was used for the following example.

Experimental Procedures:

A. Feeding of LAB Via Oral Gavage

The C57BL/6J mice as described in the section entitled "1. Experimental mice" of the General Experimental Materials were fed with the choline-deficient diet described in the same section for one week, after which the mice were randomly divided into a control group (n=9), a comparative group 1 (n=7), a comparative group 2 (n=7), and an experimental group (n=7). Thereafter, the mice were fed once a day for a total of 7 days with a diet containing 1% choline (Manufacturer: Harlan Teklad, Madison, WI, USA; Catalogue No.: TD14017). The mice in the comparative group 1, comparative group 2 and experimental group were also respectively fed, via oral gavage, with the liquid cultures of *Lactobacillus fermentum* LF1143, *Lactobacillus plantarum* LP1145 and *Lactobacillus amylovorus* LAM1345 prepared in the abovementioned section entitled "A. Preparation of liquid lactic acid bacterial (LAB) culture" of the Experimental Materials, at a volume ranging from 200 µL to 250 µL per mouse. The mice in the control group were fed, via oral gavage, with PBS in a volume ranging from 200 µL to 250 µL.

B. Preparation of Serum Sample

On the $7^{th}$ day after feeding the respective one of the liquid LAB cultures to the mice in the comparative group 1, comparative group 2, and the experimental group, and feeding PBS to the control group, and prior to feeding the diet containing 1% choline to the mice in each group, blood sample was drawn from the orbit of each mouse using a capillary tube, and then was left to stand at room temperature for 2 hours so as to undergo coagulation. Subsequently, centrifugation was conducted at a temperature of 4° C. and a speed of 2000 rpm for 10 minutes, and then filtration was performed with a filter membrane having a pore size of 0.2 µm. The serum samples thus obtained were subjected to the following analyses.

C. Determination of TMAO Concentration

The serum sample (25 µL) of the respective one of the mice in the control group, the comparative group 1, the comparative group 2, and the experimental group was added to 10 µL of 1 ppm of d9-TMAO (Manufacturer: Toronto Research Chemicals, Canada; Catalogue No.: T795792) which served as an internal standard, followed by adding 30 µL of 20 mg/mL of ethyl bromoacetate in acetonitrile which served as an derivatization reagent, and 1 µL of 26% ammonia solution, so as to obtain a mixture. Such mixture was allowed to undergo a derivatization reaction in a dark environment at room temperature for 30 minutes, followed by adding 1 mL of 50% acetonitrile (in a 0.025% formic acid solution) so as to stop the derivatization reaction. Thereafter, the thus obtained mixture was subjected to ultra performance liquid chromatography-tandem mass spectrometry (UPLC-MS/MS) analysis for measuring the TMAO concentration. In comparison, different concentrations of TMAO (Manufacturer: Toronto Research Chemicals; Canada; Catalogue No.: T795790) which ranged from 1 ppm to 6 ppm in 50% acetonitrile, and each of which served as control standard, were also subjected to the UPLC-MS/MS analysis to prepare a standard curve. The UPLC analysis was performed using AQUITY UPLC® system (Manufacturer: Waters Corporation, Milford, MA, USA), and the operating parameters and conditions thereof are summarized in Table 4 below.

TABLE 4

| Operating parameters | AQUITY UPLC system |
| --- | --- |
| Type of chromatography column | ACQUITY UPLC ® ethylene bridged hybrid (BEH) HILIC Column, size of packing material: 130Å, 1.7 µM |
| Size of chromatography column | Length: 100 mm; inner diameter: 2.1 mm |
| Operating temperature | 30° C. |
| Mobile phase | Solvent A: 95% acetonitrile (containing 0.1% formic acid and 10 mM ammonium formate buffer); Solvent B: 50% acetonitrile (containing 0.1% formic acid and 10 mM ammonium formate buffer) |
| Gradient elution of mobile phase | Solvent A was maintained at 100% at 0 to $5^{th}$ min; solvent A was changed from 100% to 25% at $5^{th}$ to $12.8^{th}$ min; solvent A was changed from 25% to 0% at $12.8^{th}$ min to $14^{th}$ min. |
| Sample injection volume (µL) | 10 |
| Flow rate (mL/min) | 0.1 |

The tandem mass spectrometry analysis was performed using Xevo® TQ-MS tandem quadrupole mass spectrometer (Manufacturer: Waters Corporation, Milford, MA, USA).

D. Statistical Analysis

Experimental data obtained from all of the groups as described in the abovementioned section entitled "C. Determination of TMAO concentration" of the Experimental Procedures are expressed as mean±standard deviation (SD), and were analyzed by one-way analysis of variance (ANOVA) and independent-samples t-test using GraphPad Prism 7.04 (Developer: GraphPad Software Inc., San Diego, CA) software to determine differences between the groups. Statistical significance is indicated by $p<0.05$.

Figure 1:
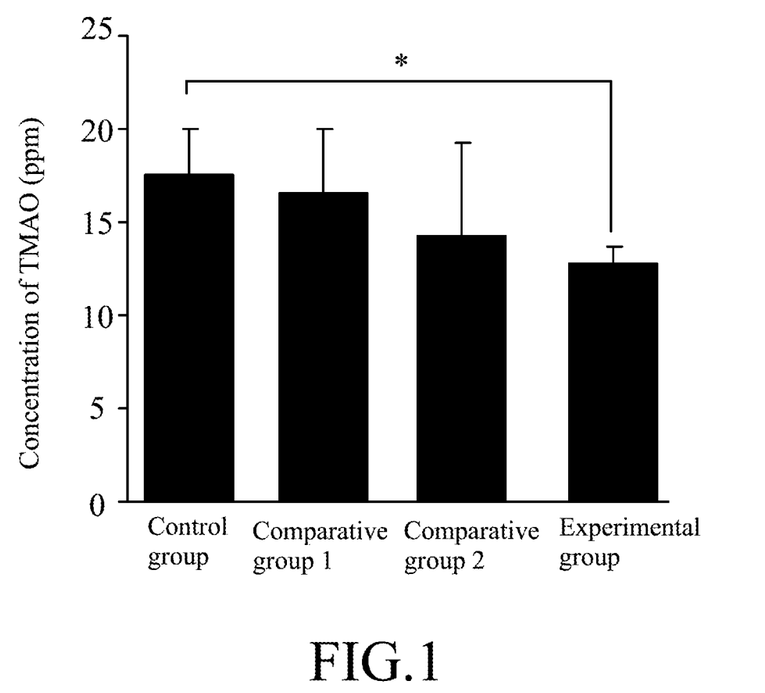
FIG. 1 shows the concentration of trimethylamine-n-oxide (TMAO) in each group of Example 2, infra, in which the symbol "*" represents p<0.05 (compared with the control group)

Results:

FIG. 1 shows the concentration of TMAO in the mouse serum on day 7 after feeding, via oral gavage, *Lactobacillus amylovorus* LAM1345 (i.e., the experimental group), *Lactobacillus fermentum* LF1143 (i.e., the comparative group 1), *Lactobacillus plantarum* LP1145 (i.e., the comparative group 2), or PBS (i.e., the control group). As shown in FIG. 1, in comparison with the control group, the concentration of TMAO in each of the comparative groups 1 and 2 was only slightly reduced, while the concentration of TMAO in the experimental group was significantly reduced, i.e., up to 28%, suggesting that *Lactobacillus amylovorus* LAM1345 of the present disclosure can effectively and rapidly reduce the concentration of TMAO in serum.

Example 3. Evaluation of Effect of LAB Mixture Containing *Lactobacillus amylovorus* LAM1345 and Other *Lactobacillus* Spp. on the Formation of Trimethylamine (TMA) and TMAO Experimental Materials:

A. Preparation of LAB Mixture

The three liquid LAB cultures prepared in the section, entitled "A. Preparation of liquid lactic acid bacteria (LAB) cultures" of the Experimental Materials of Example 2, were evenly mixed to obtain a LAB mixture containing *Lactobacillus amylovorus* LAM1345 of the present disclosure, *Lactobacillus fermentum* LF1143 and *Lactobacillus plantarum* LP1145 in a ratio of 1:1:1 (v/v/v) with a bacterial concentration ranging from $10^8$ CFU/mL to $10^{10}$ CFU/mL.

Experimental Procedures:

A. Feeding of LAB Mixture and Preparation of Serum Samples

The C57BL/6J mice fed with the choline-deficient diet for one week as described in the section entitled "1. Experimental mice" of the General Experimental Procedures were randomly divided into a control group (n=5), a comparative group (n=5), and an experimental group (n=5). The mice were fed once a day for a total of 7 days with the diet containing 1% choline as described in section A of the Experimental Procedures of Example 2. The mice in the comparative group and experimental group were also respectively fed, via oral gavage, with the liquid culture of *Lactobacillus amylovorus* LAM1345 prepared in the section entitled "A. Preparation of liquid lactic acid bacteria (LAB) cultures" of the Experimental Materials of Example 2 and the LAB mixture described in the abovementioned section entitled "A. Preparation of LAB mixture" of the Experimental Materials, at a volume ranging from 200 μL to 250 μL per mouse, while the mice in the control group were fed, via oral gavage, with PBS in a volume ranging from 200 μL to 250 μL. Thereafter, on the $7^{th}$ day, after the mice in the experimental group and the comparative group were respectively fed with the LAB mixture and the liquid culture of *Lactobacillus amylovorus* LAM1345 as described above, after the mice in the control group were fed with PBS, and prior to feeding the diet containing 1% choline to the mice of each group, serum samples were prepared from the mice of each group according to the procedures as described in the section entitled "B. Preparation of serum sample" of the Experimental Procedures of Example 2, and were subjected to the following analyses.

B. Determination of TMA and TMAO Concentrations

The concentration of TMAO in each of the serum samples was determined according to the procedures as described in the section entitled "C. Determination of TMAO concentration" of the Experimental Procedures of Example 2, while the procedures for determining the TMA concentration in each of the serum samples were similar to those of TMAO, except that 1 ppm of d9-TMA (Manufacturer: Toronto Research Chemicals; Canada; Catalogue No.: T795807) served as an internal standard, and different concentrations of TMA ranging from 1 ppm to 6 ppm in 50% acetonitrile served as control standards.

Figure 2:
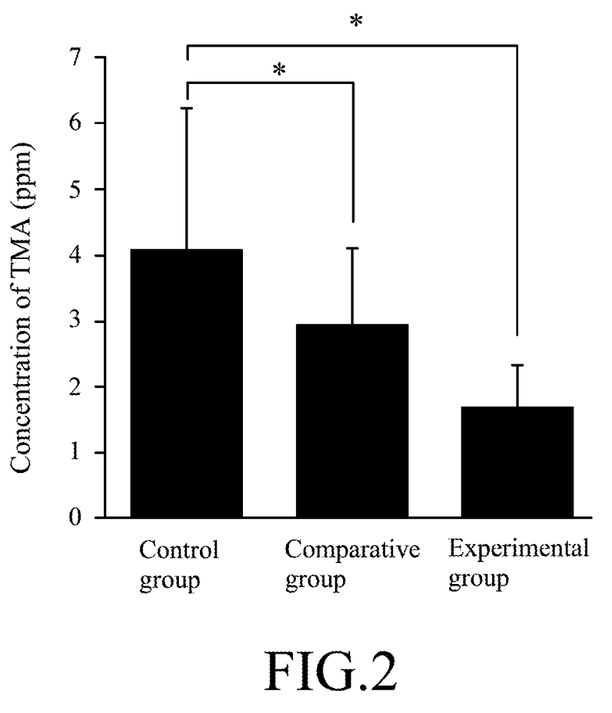
FIG. 2 shows the concentration of trimethylamine (TMA) in each group of Example 3, infra, in which the symbol "*" represents p<0.05 (compared with the control group)
Figure 3:
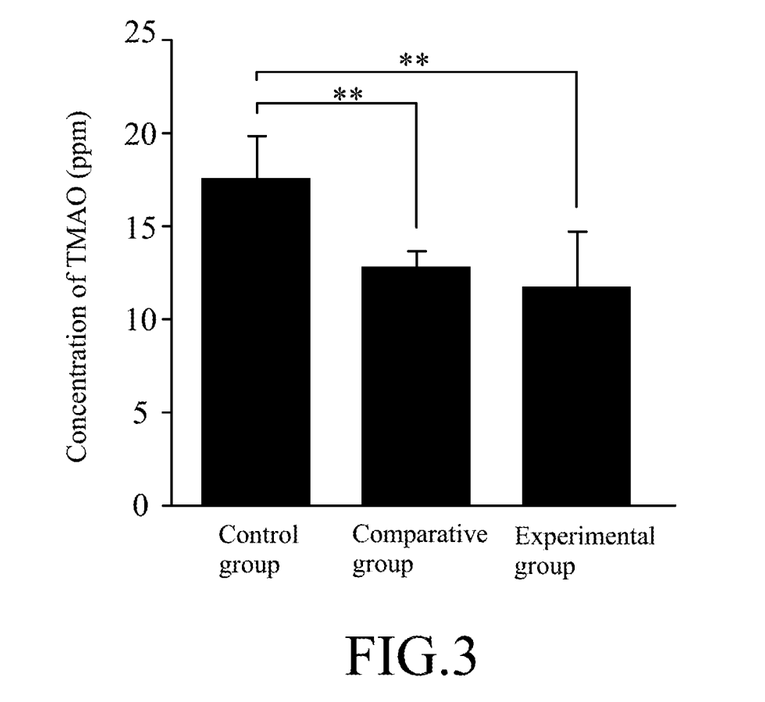
FIG. 3 shows the concentration of TMAO in each group of Example 3, infra, in which the symbol "**" represents p<0.01 (compared with the control group).

Results:

FIGS. 2 and 3 show the concentrations of TMA and TMAO, respectively, in the mouse serum on day 7 after feeding, via oral gavage, the liquid culture of *Lactobacillus amylovorus* LAM1345 of the present disclosure (i.e., the comparative group), the LAB mixture (i.e., the experimental group), and PBS (i.e., the control group). As shown in FIGS. 2 and 3, in comparison with the control group, the concentrations of TMA and TMAO of the comparative group were significantly reduced, while those of the experimental group were even more significantly reduced, suggesting that *Lactobacillus amylovorus* LAM1345 DSM 33510 of the present disclosure, either alone or in combination with other strains of *Lactobacillus* spp., is capable of effectively reducing the TMA and TMAO levels.

In summary, due to the significant reduction of the TMA level in the serum, the applicants believe that *Lactobacillus amylovorus* LAM1345 of the present disclosure is capable of effectively inhibiting the conversion of choline to TMA, thereby inhibiting the formation of TMAO. Therefore, *Lactobacillus amylovorus* LAM1345 of the present disclosure is expected to be useful for treating diseases associated with elevated TMA and/or TMAO levels, and may be further used in combination with other known probiotics to exert desirable effects.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

```
SEQUENCE LISTING
<110> SYNBIO TECH INC.

<120> LACTOBACILLUS AMYLOVORUS LAM1345 ISOLATE, COMPOSITION
INCLUDING THE SAME AND USE THEREOF

<130> PE-63922 WO

<160> 6

<170> PatentIn version 3.5

<210> 1

<211> 20

<212> DNA

<213> Artificial Sequence

<220>

<223> Forward primer for 16S rDNA

<400> 1
agagtttgat cctggctcag                                            20
```

-continued

<210> 2

<211> 18

<212> DNA

<213> Artificial Sequence

<220>

<223> Reverse primer for 16S rDNA

<400> 2
ggttaccttg ttacgact                                                    18

<210> 3

<211> 1525

<212> DNA

<213> 16S rDNA gene of Lactobacillus amylovorus LAM1345

<400> 3
tcaggacgaa cgctggcggc gtgcctaata catgcaagtc gagcgagcgg aaccaacaga      60
tttacttcgg taatgacgtt gggaaagcga gcggcggatg ggtgagtaac acgtggggaa     120
cctgccccta agtctgggat accatttgga aacaggtgct aataccggat aataaagcag     180
atcgcatgat cagcttttga aaggcggcgt aagctgtcgc taaggatggg ccccgcggtg     240
cattagctag ttggtaaggt aacggcttac caaggcgacg atgcatagcc gagttgagag     300
actgatcggc cacattggga ctgagacacg gcccaaactc ctacgggagg cagcagtagg     360
gaatcttcca caatggacgc aagtctgatg gagcaacgcc gcgtgagtga agaaggtttt     420
cggatcgtaa agctctgttg ttggtgaaga aggatagagg tagtaactgg cctttatttg     480
acggtaatca accagaaagt cacggctaac tacgtgccag cagccgcggt aatacgtagg     540
tggcaagcgt tgtccggatt tattgggcgt aaagcgagcg caggcggaaa ataagtcta     600
atgtgaaagc cctcggctta accgaggaac tgcatcggaa actgttttc ttgagtgcag     660
aagaggagag tggaactcca tgtgtagcgg tggaatgcgt agatatatgg aagaacacca     720
gtggcgaagg cggctctctg gtctgcaact gacgctgagg ctcgaaagca tgggtagcga     780
acaggattag ataccctggt agtccatgcc gtaaacgatg agtgctaagt gttgggaggt     840
ttccgcctct cagtgctgca gctaacgcat taagcactcc gcctggggag tacgaccgca     900
aggttgaaac tcaaaggaat tgacgggggc ccgcacaagc ggtggagcat gtggtttaat     960
tcgaagcaac gcgaagaacc ttaccaggtc ttgacatcta gtgcaatctg tagagatacg    1020
gagttccctt cggggacgct aagacaggtg gtgcatggct gtcgtcagct cgtgtcgtga    1080
gatgttgggt taagtcccgc aacgagcgca acccttgtta ttagttgcca gcattaagtt    1140
gggcactcta atgagactgc cggtgacaaa ccggaggaag gtgggatga cgtcaagtca    1200
tcatgcccct tatgacctgg gctacacacg tgctacaatg gcagtacaa cgagaagcaa    1260
gcctgcgaag gcaagcgaat ctctgaaagc tgttctcagt tcggactgca gtctgcaact    1320
cgactgcacg aagctggaat cgctagtaat cgcggatcag cacgccgcgg tgaatacgtt    1380
cccgggcctt gtacacaccg cccgtcacac catgggagtc tgcaatgccc aaagccggtg    1440
gcctaacctt cgggaaggag ccgtctaagg cagggcagat gactggggtg aagtcgtaac    1500
aaggtagccg taggagaacc tgcgg                                          1525

-continued

<210> 4

<211> 23

<212> DNA

<213> Artificial Sequence

<220>

<223> Forward primer for lepA gene

<220>

<221> misc_feature

<222> (3) . . . (3)

<223> d represents a, g or t

<220>

<221> misc_feature

<222> (9) . . . (9)

<223> r represents g or a

<220>

<221> misc_feature

<222> (12) . . . (12)

<223> y represents t or c

<220>

<221> misc_feature

<222> (15) . . . (15)

<223> y represents t or e

<220>

<221> misc_feature

<222> (18) . . . (18)

<223> w represents a or t

<220>

<221> misc_feature

<222> (21) . . . (21)

<223> y represents t or c

<400> 4
ggdcacgtrg ayttytcwta yga          23

<210> 5

<211> 23

<212> DNA

<213> Artificial Sequence

<220>

<223> Reverse primer for lepA gene

<220>

<221> misc_feature

```
<222> (6) ... (6)
<223> v represents a, g or c
<220>
<221> misc_feature
<222> (9) ... (9)
<223> y represents t or c
<220>
<221> misc_feature
<222> (12) ... (12)
<223> n represents a, g, c or t
<220>
<221> misc_feature
<222> (15) ... (15)
<223> d represents a, g or t
<220>
<221> misc_feature
<222> (16) ... (16)
<223> r represents g or a
<220>
<221> misc_feature
<222> (18) ... (18)
<223> w represents a or t
<400> 5
gcatavccyt tngtdrawga ctt                                          23

<210> 6
<211> 1009
<212> DNA
<213> lepA gene of Lactobacillus amylovorus LAM1345

<400> 6
cacaaggtgt gcaagctcag actttggcta acacttactt agcgatcgat gatgatttgg    60
caatttacc tgtaattaat aagatcgact tgccatctgc tgatattcct aagactaagg    120
aagaaattga agagatgctt ggtcttgatg cttctgaagc tgcggaagtt tctggtaaaa   180
ccggtcaagg catcaaggac atgctggaaa aagtagtaaa agacattcca gctccatctg   240
gtgatattac tgcgccactc aaggctttga tttttgactc aaaatatgat gactatcgtg   300
gtgtcgtaat gtcagtcaaa atcgaagacg gtacagttaa gcctggtgac cgagttcaaa   360
ttatgaatac tggtaaggaa tatgaagtta cagaagtagg tgtttcaagt ccacatccaa   420
ttaagaagga tatcttgatt gctggggatg taggttatat tactgccaac attaagtccg   480
tacgtgaaac tcgtgttggt gatactatca cccaagcaga taatcctact gccgaaccac   540
ttccaggtta ccgtcaaatt ccaccaatgg tttactctgg tatgtatcca gttgataacc   600
gtgattatga agacttaaag gaagcttgc aaaagttgca attaaacgat gcagctttag   660
aatttgaacc tgaaacttct actgctttag gcttcgggtt ccgttgtggt ttcttaggac   720
```

-continued

```
ttttgcatat ggatgttgtg caagaacgac tagaacaaga atttgatctt gatttaatta      780
tgactgcacc atccgttgac tatcatgcaa ttatgaatga tggctcaact aaggtaattg      840
ataacccatc agatttgcca gatgctggtg aatacaagga agtgcaagag ccttatgtta      900
aggcagaaat tatggtgcca aatgactttg ttggccctgt aatggaactt tgtcaaagaa      960
aacgtggcga atttgttacg atggactatc ttgataagta ccgcgttaa               1009
```

---

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Forward primer for 16S rDNA

<400> SEQUENCE: 1
agagtttgat cctggctcag                                                   20

<210> SEQ ID NO 2
<211> LENGTH: 18
<212> TYPE: DNA
<213> ORGANISM: Artificial Sequence
<220> FEATURE:
<223> OTHER INFORMATION: Reverse primer for 16S rDNA

<400> SEQUENCE: 2
ggttaccttg ttacgact                                                     18

<210> SEQ ID NO 3
<211> LENGTH: 1525
<212> TYPE: DNA
<213> ORGANISM: Lactobacillus amylovorus

<400> SEQUENCE: 3
tcaggacgaa cgctggcggc gtgcctaata catgcaagtc gagcgagcgg aaccaacaga       60
tttacttcgg taatgacgtt gggaaagcga gcggcggatg ggtgagtaac acgtggggaa      120
cctgccccta agtctgggat accatttgga aacaggtgct aataccggat aataaagcag      180
atcgcatgat cagcttttga aaggcggcgt aagctgtcgc taagggatgg ccccgcggtg      240
cattagctag ttggtaaggt aacggcttac caaggcgacg atgcatagcc gagttgagag      300
actgatcggc cacattggga ctgagacacg gcccaaactc ctacgggagg cagcagtagg      360
gaatcttcca caatggacgc aagtctgatg agcaacgcc gcgtgagtga agaaggtttt       420
cggatcgtaa agctctgttg ttggtgaaga aggatagagg tagtaactgg cctttatttg      480
acggtaatca accagaaagt cacggctaac tacgtgccag cagccgcggt aatacgtagg      540
tggcaagcgt tgtccggatt tattgggcgt aaagcgagcg caggcggaaa ataagtcta       600 atgtgaaagc cctcggctta accgaggaac tgcatcggaa actgttttc ttgagtgcag       660 aagaggagag tggaactcca tgtgtagcgg tggaatgcgt agatatatgg aagaacacca      720
gtggcgaagg cggctctctg gtctgcaact gacgctgagg ctcgaaagca tgggtagcga      780
acaggattag ataccctggt agtccatgcc gtaaacgatg agtgctaagt gttgggaggt      840
ttccgcctct cagtgctgca gctaacgcat taagcactcc gcctgggag tacgaccgca       900 aggttgaaac tcaaaggaat tgacggggc ccgcacaagc ggtggagcat gtggtttaat       960
```

```
tcgaagcaac gcgaagaacc ttaccaggtc ttgacatcta gtgcaatctg tagagatacg    1020
gagttcccct cggggacgct aagacaggtg gtgcatggct gtcgtcagct cgtgtcgtga    1080
gatgttgggt taagtcccgc aacgagcgca acccttgtta ttagttgcca gcattaagtt    1140
gggcactcta atgagactgc cggtgacaaa ccggaggaag gtggggatga cgtcaagtca    1200
tcatgcccct tatgacctgg gctacacacg tgctacaatg gcagtacaa cgagaagcaa     1260 gcctgcgaag gcaagcgaat ctctgaaagc tgttctcagt tcggactgca gtctgcaact    1320
cgactgcacg aagctggaat cgctagtaat cgcggatcag cacgccgcgg tgaatacgtt    1380
cccgggcctt gtacacaccg cccgtcacac catgggagtc tgcaatgccc aaagccggtg    1440
gcctaacctt cgggaaggag ccgtctaagg cagggcagat gactggggtg aagtcgtaac    1500
aaggtagccg taggagaacc tgcgg                                          1525
```

<210> SEQ ID NO 4
<211> LENGTH: 23
<212> TYPE: DNA
<213> ORGANISM: Artificial Sequence
<220> FEATURE:
<223> OTHER INFORMATION: Forward primer for lepA gene
<220> FEATURE:
<221> NAME/KEY: misc_feature
<222> LOCATION: (3)..(3)
<223> OTHER INFORMATION: d represents a, g or t
<220> FEATURE:
<221> NAME/KEY: misc_feature
<222> LOCATION: (9)..(9)
<223> OTHER INFORMATION: r represents g or a
<220> FEATURE:
<221> NAME/KEY: misc_feature
<222> LOCATION: (12)..(12)
<223> OTHER INFORMATION: y represents t or c
<220> FEATURE:
<221> NAME/KEY: misc_feature
<222> LOCATION: (15)..(15)
<223> OTHER INFORMATION: y represents t or c
<220> FEATURE:
<221> NAME/KEY: misc_feature
<222> LOCATION: (18)..(18)
<223> OTHER INFORMATION: w represents a or t
<220> FEATURE:
<221> NAME/KEY: misc_feature
<222> LOCATION: (21)..(21)
<223> OTHER INFORMATION: y represents t or c

<400> SEQUENCE: 4
ggdcacgtrg ayttytcwta yga                                              23

<210> SEQ ID NO 5
<211> LENGTH: 23
<212> TYPE: DNA
<213> ORGANISM: Artificial Sequence
<220> FEATURE:
<223> OTHER INFORMATION: Reverse primer for lepA gene
<220> FEATURE:
<221> NAME/KEY: misc_feature
<222> LOCATION: (6)..(6)
<223> OTHER INFORMATION: v represents a, g or c
<220> FEATURE:
<221> NAME/KEY: misc_feature
<222> LOCATION: (9)..(9)
<223> OTHER INFORMATION: y represents t or c
<220> FEATURE:
<221> NAME/KEY: misc_feature
<222> LOCATION: (12)..(12)
<223> OTHER INFORMATION: n represents a, g, c or t
<220> FEATURE:
<221> NAME/KEY: misc_feature
<222> LOCATION: (15)..(15)

```
<223> OTHER INFORMATION: d represents a, g or t
<220> FEATURE:
<221> NAME/KEY: misc_feature
<222> LOCATION: (16)..(16)
<223> OTHER INFORMATION: r represents g or a
<220> FEATURE:
<221> NAME/KEY: misc_feature
<222> LOCATION: (18)..(18)
<223> OTHER INFORMATION: w represents a or t

<400> SEQUENCE: 5
gcatavccyt tngtdrawga ctt                                       23

<210> SEQ ID NO 6
<211> LENGTH: 1009
<212> TYPE: DNA
<213> ORGANISM: Lactobacillus amylovorus

<400> SEQUENCE: 6
cacaaggtgt gcaagctcag actttggcta acacttactt agcgatcgat gatgatttgg    60
caattttacc tgtaattaat aagatcgact tgccatctgc tgatattcct aagactaagg   120
aagaaattga agagatgctt ggtcttgatg cttctgaagc tgcggaagtt tctggtaaaa   180
ccggtcaagg catcaaggac atgctggaaa agtagtaaa agacattcca gctccatctg   240
gtgatattac tgcgccactc aaggctttga tttttgactc aaaatatgat gactatcgtg   300
gtgtcgtaat gtcagtcaaa atcgaagacg gtacagttaa gcctggtgac cgagttcaaa   360
ttatgaatac tggtaaggaa tatgaagtta cagaagtagg tgtttcaagt ccacatccaa   420
ttaagaagga tatcttgatt gctggggatg taggttatat tactgccaac attaagtccg   480
tacgtgaaac tcgtgttggt gatactatca cccaagcaga taatcctact gccgaaccac   540
ttccaggtta ccgtcaaatt ccaccaatgg tttactctgg tatgtatcca gttgataacc   600
gtgattatga agacttaaag gaagctttgc aaaagttgca attaaacgat gcagctttag   660
aatttgaacc tgaaacttct actgctttag gcttcgggtt ccgttgtggt ttcttaggac   720
ttttgcatat ggatgttgtg caagaacgac tagaacaaga atttgatctt gatttaatta   780
tgactgcacc atccgttgac tatcatgcaa ttatgaatga tggctcaact aaggtaattg   840
ataacccatc agatttgcca gatgctggtg aatacaagga agtgcaagag ccttatgtta   900
aggcagaaat tatggtgcca aatgactttg ttggccctgt aatggaactt tgtcaaagaa   960
aacgtggcga atttgttacg atggactatc ttgataagta ccgcgttaa            1009
```

What is claimed is:

1. A method for treating a disease associated with at least an elevated one of trimethylamine (TMA) and trimethylamine-n-oxide (TMAO) levels, comprising:

administering, to a subject in need thereof, a pharmaceutical composition consisting of an isolated strain of *Lactobacillus* amylovorus LAM1345, which is deposited at Deutsche Sammlung von Mikroorganismen und Zellkulturen GmbH under an accession number DSM 33510; and a pharmaceutically acceptable carrier.

2. The method as claimed in claim 1, wherein the pharmaceutical composition is in a dosage form for oral administration.

3. A method of reducing a level of trimethylamine (TMA) and/or a level of trimethylamine-n-oxide (TMAO), comprising:

administering, to a subject in need thereof, a pharmaceutical composition consisting of an isolated strain of *Lactobacillus* amylovorus LAM1345, which is deposited at Deutsche Sammlung von Mikroorganismen und Zellkulturen GmbH under an accession number DSM 33510; and a pharmaceutically acceptable carrier, wherein the isolated strain of *Lactobacillus* amylovorus LAM1345 is effective for reducing the level of trimethylamine (TMA) and/or a level of trimethylamine-n-oxide (TMAO) in the subject as compared to that of where the isolated strain of *Lactobacillus* amylovorus LAM1345 is not administered to the subject.

* * * * *